(12) United States Patent
Spiegel

(10) Patent No.: US 11,650,434 B2
(45) Date of Patent: May 16, 2023

(54) OPTICAL SYSTEMS, SPECTACLE LENS AND EYEWEAR INCLUDING THE SAME

(71) Applicant: Essilor International, Charenton-le-Pont (FR)

(72) Inventor: Daniel Spiegel, Singapore (SG)

(73) Assignee: Essilor International, Charenton-le-Pont (FR)

( * ) Notice: Subject to any disclaimer, the term of this patent is extended or adjusted under 35 U.S.C. 154(b) by 95 days.

(21) Appl. No.: 17/258,065

(22) PCT Filed: Jul. 19, 2019

(86) PCT No.: PCT/EP2019/069486
§ 371 (c)(1),
(2) Date: Jan. 5, 2021

(87) PCT Pub. No.: WO2020/025355
PCT Pub. Date: Feb. 6, 2020

(65) Prior Publication Data
US 2021/0231979 A1    Jul. 29, 2021

(30) Foreign Application Priority Data
Jul. 31, 2018   (EP) ........................................ 8306034

(51) Int. Cl.
*G02C 11/04* (2006.01)
*A61N 5/06* (2006.01)

(52) U.S. Cl.
CPC ............ *G02C 11/04* (2013.01); *A61N 5/0618* (2013.01); *A61N 5/0622* (2013.01); *A61N 2005/0629* (2013.01); *A61N 2005/0648* (2013.01); *A61N 2005/0652* (2013.01); *A61N 2005/0663* (2013.01); *A61N 2005/0666* (2013.01); *A61N 2005/0667* (2013.01)

(58) Field of Classification Search
CPC ........ G02C 11/04; G02C 7/086; G02C 7/104; G02C 2202/10; G02C 2202/24;
(Continued)

(56) References Cited

U.S. PATENT DOCUMENTS 10,881,550 B2   1/2021   Tedford et al.
2010/0217358 A1   8/2010   Hebert et al.
(Continued)

FOREIGN PATENT DOCUMENTS

CN   105431201 A   3/2016
CN   107072821 A   8/2017

OTHER PUBLICATIONS

Cakmakci, O. et al., "Head-Worn Displays: A Review," Journal of Display Technology, vol. 2, No. 3, Sep. 2006, XP007911184, pp. 199-216.
(Continued)

*Primary Examiner* — Joseph M Dietrich
*Assistant Examiner* — Michael T. Holtzclaw
(74) *Attorney, Agent, or Firm* — Oblon, McClelland, Maier & Neustadt, L.L.P.

(57) ABSTRACT

An illumination system adapted for an eyewear that includes a light source configured to emit a first light including a power spectrum having full width at half maximum of less than 100 nm in a first range of wavelengths and a second light including a power spectrum having full width at half maximum of less than 100 nm in a second range of wavelengths, the power spectrum of the first light and the power spectrum of the second light differ from each other, and the light source is further configured to emit pulses of light with a pre-determined time function. The pre-determined time function comprises a plurality of packets, each packet of the plurality of packets being followed by a packet interval, and each packet including a pulse alternation between a pulse of the first light and a pulse of the second light.

13 Claims, 14 Drawing Sheets

(58) Field of Classification Search
CPC .............. A61N 5/0618; A61N 5/0622; A61N 2005/0629; A61N 2005/0648; A61N 2005/0652; A61N 2005/0663; A61N 2005/0666; A61N 2005/0667; A61N 2005/0662; A61M 2021/0044; A61M 2205/502; A61M 2205/587; A61M 2209/088; A61M 21/00; G02B 2027/0112; G02B 2027/0178; G02B 27/017

See application file for complete search history.

(56) References Cited

U.S. PATENT DOCUMENTS

| | | | |
|---|---|---|---|
| 2012/0215291 A1 | 8/2012 | Pugh et al. | |
| 2013/0278887 A1* | 10/2013 | Legerton | G02C 7/049 351/158 |
| 2016/0144149 A1 | 5/2016 | Pugh et al. | |
| 2016/0158486 A1* | 6/2016 | Colbaugh | A61N 5/0618 607/88 |
| 2016/0158487 A1 | 6/2016 | Colbaugh et al. | |
| 2017/0173361 A1 | 6/2017 | Hebert et al. | |
| 2017/0357107 A1 | 12/2017 | Rousseau et al. | |
| 2018/0074322 A1 | 3/2018 | Rousseau et al. | |
| 2018/0280718 A1* | 10/2018 | Tsubota | A61H 5/00 |
| 2018/0345034 A1* | 12/2018 | Butzloff | A61N 5/0618 |
| 2021/0329764 A1* | 10/2021 | Linder | G02C 11/10 |

OTHER PUBLICATIONS

International Search Report and Written Opinion issued on Oct. 7, 2019 in PCT/EP2019/069486 filed on Jul. 19, 2019.
Combined Chinese Office Action and Search Report dated Mar. 30, 2022 in Chinese Patent Application No. 201980050610.3 (with English translation), 16 pages.

* cited by examiner

A - A

A)

B)

C)

Time

■ State 1
▨ State 2
☐ Clear state

OPTICAL SYSTEMS, SPECTACLE LENS AND EYEWEAR INCLUDING THE SAME

TECHNICAL FIELD

This disclosure relates to optical systems, a spectacle lens and an eyewear including the same.

BACKGROUND

There are around 23% myopic people worldwide and the estimates are that by 2050 this number will increase to 50%. Myopia is associated with vision deficiency. In addition, pathological myopia is associated with severe vision deficits and in extreme cases with blindness. Thus, myopia control has become a serious concern both in the clinical and research domains of eye care.

In light of the above, there remains a need for systems, which may be used in myopia control.

SUMMARY

Generally, a system is provided, which is adapted for an eyewear and/or a spectacle lens. The system may be configured to actively control an amount of light at a point at a predetermined distance of the system, for example to switch between a first light intensity and a second light intensity. The disclosure also provides for a spectacle lens, which may include the system. The disclosure also provides for an eyewear, which may include the system.

The system may be an illumination system and/or an optical filter system.

In a first aspect, an illumination system, adapted for an eyewear, is provided. The illumination system may include a light source configured to emit a first light. The first light may include a power spectrum having full width at half maximum (FWHM) of less than 100 nm, for example selected from 10 nm to 100 nm, in a first range of wavelengths. The light source may be further configured to emit a second light comprising a power spectrum having full width at half maximum of less than 100 nm, for example selected from 10 nm to 100 nm, in a second range of wavelengths. Further, the power spectrum of the first light and the power spectrum of the second light may differ from each other. The light source may be further configured to emit pulses of light. The pulses of light may include a pre-determined time function. The pre-determined time function may include a plurality of packets followed by packet intervals. Each packet of the plurality of packets may be followed by a packet interval. Each packet may comprise a pulse alternation between a pulse of the first light and a pulse of the second light.

In various embodiments according to the first aspect, the emission spectrum of the second light has no peak in the first range of wavelengths.

In various embodiments according to the first aspect, the pulse alternation may be repeated two or more times.

In various embodiments according to the first aspect, the first range of wavelengths may be between 450 nm and 495 nm.

In various embodiments according to the first aspect, the second range of peak wavelengths may be between 620 nm and 750 nm.

In various embodiments according to the first aspect, the pre-determined time function may include a sequence of a plurality of pulses of the first light with a first pulse duration; and may further include an interval between two consecutive pulses of the plurality of pulses.

In various embodiments according to the first aspect, the pulse alternation may further include an interval between consecutive pulses of the first light and the second light.

In various embodiments according to the first aspect, the duration of each packet may be in the range of 1-5 seconds, preferably 2 seconds.

In various embodiments according to the first aspect, the duration of each packet interval may be in the range of 5-20 seconds, preferably 8 seconds.

In various embodiments according to the first aspect, the illumination system may further include a button, for example an electrical button. The button may be configured to switch the light source between at least an active mode and an inactive mode. In the active mode, the light source may emit pulses of light with the pre-determined time function. In the inactive mode, the light source does not emit light.

In a second aspect, an eyewear is provided. The eyewear may include a spectacle frame and the illumination system according to various embodiments according to the first aspect.

In various embodiments according to the second aspect, the eyewear may further include at least one spectacle lens or optionally a pair of spectacle lenses including the one lens, mounted on the spectacle frame.

In various embodiments according to the second aspect, the light source of the illumination system may be mounted on the spectacle frame or on the spectacle lens of the eyewear.

In various embodiments according to the second aspect, the light source of the illumination system may be configured to emit light in a direction to a wearer's eye, when the wearer is wearing the eyewear.

In various embodiments according to the second aspect, the light source of the illumination system and the spectacle lens may be configured so that light emitted by the light source of the illumination system is at least partially reflected by the spectacle lens, in a direction to a wearer's eye, when the wearer is wearing the pair of spectacles.

In various embodiments according to the second aspect, the spectacle lens may be configured to be at least partially reflective in the first range of wavelengths.

In various embodiments according to the second aspect, the spectacle lens may be configured to be at least partially reflective in the second range of wavelengths.

In a third aspect, an optical filter system, adapted for a spectacle lens, is provided. The optical filter system may include a band-cut filter. The band-cut filter may be configured to be in a band-cut filter state under a low light condition and not in the band-cut filter state under a high light condition. In the band-cut filter state, the filter may include a band-cut filter spectrum including a cut band. According to various embodiments, the low light condition may be a low blue light condition, which low blue light condition is when an incident light intensity, within the range of wavelength of the blue light, is equal to or lower than a light intensity threshold. According to various embodiments, the high light condition may be a high blue light condition, which high blue light condition is when the incident light intensity, within the range of wavelength of the blue light, is higher than the light intensity threshold.

In various embodiments according to the third aspect, the cut band may encompass the wavelengths of 450 nm to 495 nm. For example the cut band may be limited to the range of wavelengths from 450 nm to 494 nm.

In various embodiments according to the third aspect, the optical filter may further include a band-pass filter. The band-pass filter may be configured to be in a band-pass filter state under the high blue light condition and not in the band-pass filter state under the low blue light condition. In the band-pass filter state, the band-pass filter may include a band-pass filter spectrum including a pass band.

In various embodiments according to the third aspect, the pass band encompasses the wavelengths of 450 nm to 495 nm, for example, it may encompass the wavelengths of 460 nm to 484 nm.

In various embodiments according to the third aspect, the pass band and the cut band at least partially overlap.

In various embodiments according to the third aspect, the wavelength range of the incident light intensity may at least partially overlap with the wavelength range of: the cut band, or of the pass band, or of the cut band and the pass band.

In various embodiments according to the third aspect, the optical filter system may further include a sensor configured to detect the incident light intensity. The sensor may be configured to measure the light intensity within the range of wavelength of the blue light.

In various embodiments according to the third aspect, the optical filter system may further include a circuit electrically coupled to the sensor. The circuit may be coupled to the band-cut filter. The circuit may further be configured to set the band-cut filter in or out of the band-cut filter state, for example in accordance with the light intensity threshold. Alternatively or in addition, the circuit may be coupled to the band-pass filter and may further be configured to set the band-pass filter in or out of the band-pass filter state in accordance with the light intensity threshold. The circuit configured to set the band-pass filter may be a separate circuit or part of a common circuit in common with the circuit configured to set the band-cut filter.

In various embodiments according to the third aspect, the light intensity threshold may be in the range from 0.33 cd/m$^2$ to 44.4 cd/m$^2$, for example in the range from 5 cd/m$^2$ to 20 cd/m$^2$.

In various embodiments according to the third aspect, the light intensity threshold may be adjustable.

In various embodiments according to the third aspect, the band-cut filter may include a band-cut filter passive zone and a band-cut filter active zone. The band-cut filter active zone may be provided at a periphery of the band-cut filter passive zone.

In various embodiments according to the third aspect, the band-pass filter includes a band-pass filter passive zone and a band-pass filter active zone. The band-pass filter active zone may be provided at a periphery of the band-pass filter passive zone.

In a fourth aspect, a spectacle lens is provided according to various embodiments according to the third aspect.

In a fifth aspect, an eyewear is provided according to various embodiments according to the third aspect. The eyewear may include the optical filter system according to the third aspect.

In various embodiments according to the fifth aspect, the eyewear may further include a spectacle frame. The eyewear may further include the sensor. Alternatively, the eyewear may include the sensor, the sensor being a spectacle frame integrated sensor, wherein the sensor is integrated into the spectacle frame.

BRIEF DESCRIPTION OF THE DRAWINGS

Embodiments of the invention will now be described, by way of example only, and with reference to the following drawings in which:

FIG. 1 to FIG. 2D are examples of the first aspect of the disclosure. FIG. 3 and FIG. 4 are examples of the second aspect of the disclosure. FIG. 5 and FIG. 6 are examples of the third aspect of the disclosure. FIG. 7A and FIG. 7B are examples to a fifth aspect of the disclosure. FIG. 8 to FIG. 9 are examples relating to all aspects of the disclosure. FIG. 10A and FIG. 10B relate to the third to fifth aspects of the disclosure. Embodiments of different aspects of the present disclosure may be combined, for example the illumination system of the first aspect may be combined with the optical filter system of the third aspect, for example in a single eyewear, for example on a single spectacle frame. Also, features of embodiments of certain aspects, may be combined with embodiments of other aspects.

DETAILED DESCRIPTION

Figure 1A:
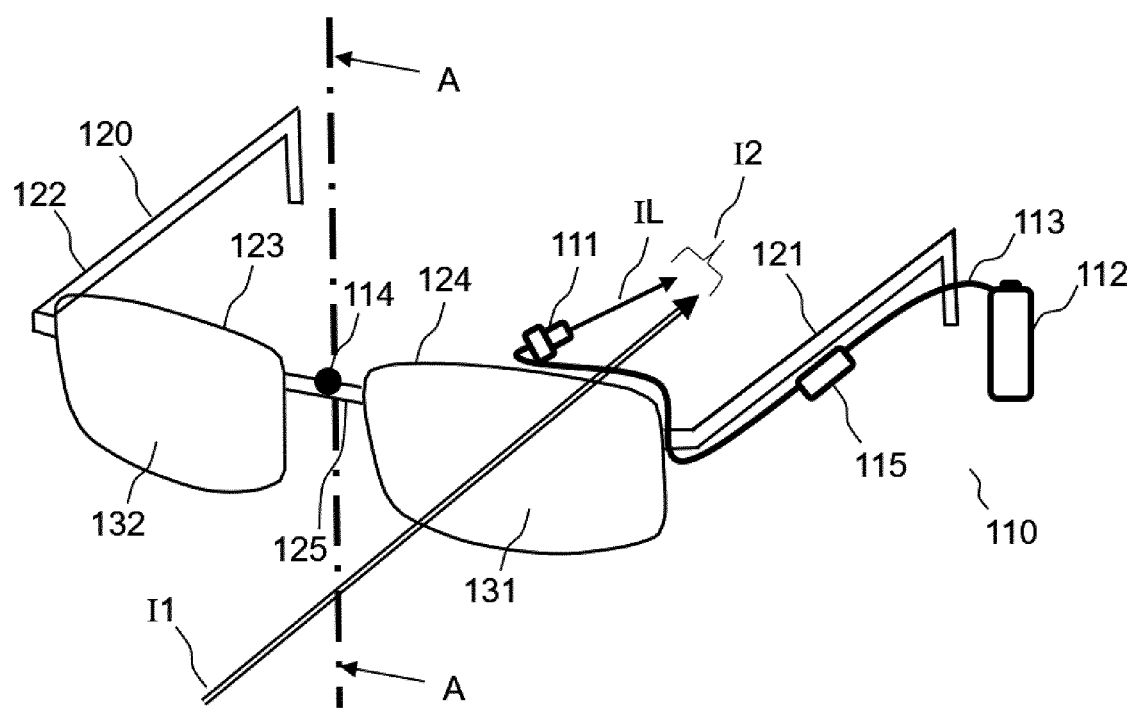
FIG. 1A is an example of an illumination system 110 on a spectacle frame 120, in accordance to various embodiments of the first aspect.

In the description, which follows, the drawing figures are not necessarily to scale and certain features may be shown in generalized or schematic form in the interest of clarity and conciseness or for informational purposes. In addition, although making and using various embodiments are discussed in detail below, it should be appreciated that as described herein are provided many inventive concepts that may be embodied in a wide variety of contexts. Embodiments discussed herein are merely representative and do not limit the scope of the invention.

Various embodiments disclosed herein relate to optical systems, spectacle lens and eyewear including the same.

The term "eyewear", according to various embodiments, may refer to an object to be wear on/in relation to the eye, for example a pair of spectacles, or a contact lens.

The term "lens" (lenses), according to various embodiments, may refer to an eyeglass (eyeglasses), which may or may not have corrective power.

As used herein, a term or expression in singular followed by an "s" in parenthesis means the term or expression in singular or plural. For example, "LED(s)" means LED or LEDs.

Blue light according to various embodiments may refer to light with wavelength in the range from 450 nm to 495 nm, for example having substantially no light with wavelength out of that range. The term "substantially" in this context may mean less than e.g. less than 10% of the total luminous intensity per unit of area (e.g. $cd/m^2$).

As used herein, the term "and/or" includes any and all combinations of one or more of the associated listed items.

Generally, a system is provided, which is adapted for an eyewear and/or a spectacle lens. The system may be configured to actively control an amount of light at a point at a predetermined distance of the system, for example to switch between a first light intensity and a second light intensity. For example, the system may be configured for varying the level of blue light reaching the eye. The disclosure also provides for a spectacle lens, which spectacle lens may include the system. The disclosure also provides for an eyewear, which eyewear may include the system.

Various embodiments may provide for a higher intensity of light under certain wavelength, for example blue light, to reach a person's eye. Various embodiments may be used in myopia control. For example, it can be used by children or young adults who are at risk of developing/progression of myopia. Various embodiments may also be applied in other conditions when intrinsic photosensitive ganglion cells' (ipRGCs) activity needs to be manipulated. One example could be people with sleep disorders as the ipRGCs may also be involved in regulation of the circadian rhythms. The symptoms of these people may be linked to dysfunction of the ipRGC and therefore could benefit from both active and passive treatments. People prone to develop migraines may also benefit from this innovation as the ipRGCs may be involved in triggering/exacerbating migraines. Other exemplary conditions may be selected from: sleep disorders, jet lag, migraines, light sensitivity, headaches, traumatic brain injury, visual fatigue, hyperopia, glare reduction.

In a first aspect, the first light, e.g. blue light, may be actively emitted by a light source, the light emission may be pulsed. The intermittent stimulation caused by pulsed light could create an increased variation of the first light (e.g. blue light) reaching a wearer's eye. For example, a wearer could receive the first light as further light in addition to ambient light under the high blue light condition. For example under high level blue light environment, additional blue light could be provided by the light source. Therefore, the variation of light intensity in the first light spectrum, e.g. of blue light, may be increased.

In the third aspect, the system may be configured to change a transmission spectrum between band-cut to band-pass, for example between blue-cut and blue-pass, so that when there is more light available, for example over a light intensity threshold, more light in a determined spectrum light may pass (for example, more blue light), and when there is less light available, for example under a light intensity threshold, light in the determined spectrum, for example, less blue light may pass. For example, a wearer would be further deprived of blue light in low blue light conditions, and the variation between a low level blue light environment and high level blue light environment will be also increased, because more blue light is cut for low blue light level environment. Therefore, the variation of blue light reaching a wearer's eye is increased. The determined spectrum may depend on the ambient light and the state of the band-pass filter and band-cut filter, so far they are provided.

The third and fifth aspects may be combined, for example to intensify the variation in light intensity, e.g. blue light intensity, which may reach a wearer's eye.

In a first aspect, an illumination system, adapted for an eyewear, is provided.

FIG. 1A shows an example of an illumination system 110 on a spectacle frame 120, in accordance to various embodiments of the first aspect. The illumination system 110 may include a light source 111 configured to emit a first light (IL), for example a light emitting diode (LED). The first light may include a power spectrum having FWHM of less than 100 nm, for example selected from 10 nm to 100 nm, in a first range of wavelengths. The light source may be further configured to emit pulses of light. The pulses of light may include a pre-determined time function.

The illumination system 110 may further include a power source 112 which may be electrically couple to the light source, for example via a conductor (e.g. conducting wires) 113. The system may further include a button 115. The system may also include a sensor 114.

FIG. 1A shows that the illumination system 110 is coupled to an eyewear. As illustrated by means of example in FIG. 1A, the eyewear may include a spectacle frame 120. The spectacle frame 120 may include a bridge 125 connecting to lenses 131 and 132 and/or rims for lenses 123 and 124, and my further include a pair of earpieces 121 and 122.

Figure 1B:
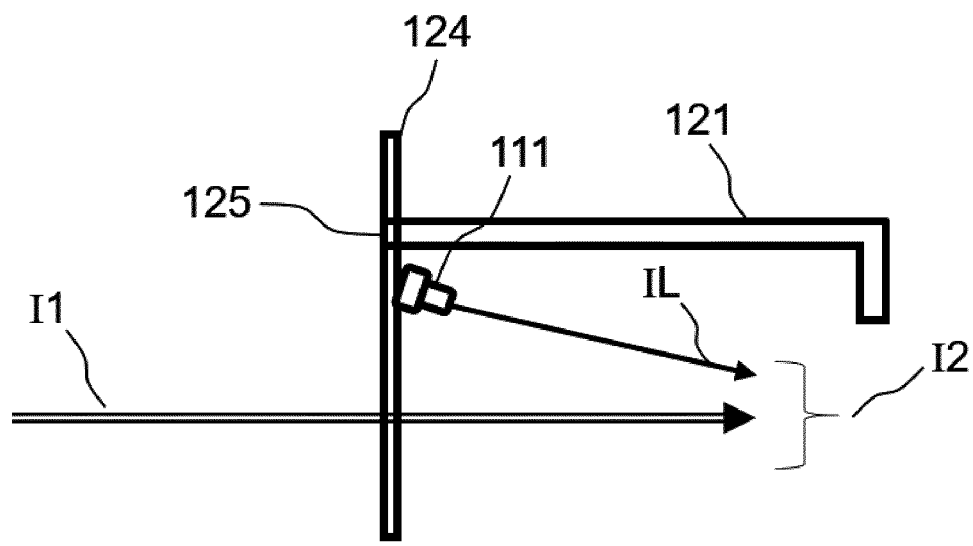
FIG. 1B is the cross sectional view A-A of FIG. 1A.

FIG. 1B is the cross sectional view A-A of FIG. 1A. As can be seen in FIG. 1A and FIG. 1B, the first light source is configured to emit a first light (IL). At a pre-determined position, the total light intensity may be I2, which may be the addition of the light intensity of the first light (IL) and of incident light (for example ambient light) with incident light intensity I1. Incident light I1 may be, as illustrated by means of example, light that is crossing lens 131 or rim for lens 124.

In various embodiments according to the first aspect, the light source may be further configured to emit a second light including an emission spectrum, having no peak in the first range of wavelengths.

In various embodiments according to the first aspect, the emission spectrum of the second light may include a power spectrum having FWHM of less than 100 nm, for example selected from 10 nm to 100 nm, in a second range of wavelengths. Further, the power spectrum of the first light and the power spectrum of the second light may differ from each other.

For example, the light source may include a second LED. For example, the light source may include a component with two integrated LEDs, the first LED configured to emit the first light and the second LED configured to emit the second light.

In various embodiments according to the first aspect, the first range of wavelengths may be between 450 nm and 495 nm. For example, the first LED may be a blue emitting LED, for example with a single emission peak. The blue emission peak may be selected in the range of between 460 nm and 490 nm.

In various embodiments according to the first aspect, the second range of peak wavelengths may be between 620 nm and 750 nm. For example, the second LED may be a red emitting LED, for example with a single emission peak. The red emission peak may be selected in the range of between 620 nm and 645 nm.

In various embodiments according to the first aspect, the pre-determined time function may include a sequence of a plurality of pulses of the first light. For example, each pulse may have a first pulse duration. The pre-determined time function may further include an interval between two consecutive pulses of the plurality of pulses.

According to various embodiments a pulse duration, for example a first pulse duration or a second pulse duration may be selected for example from 0.2 seconds to 20 seconds, for example from 0.3 seconds to 10 seconds.

Figure 2A:
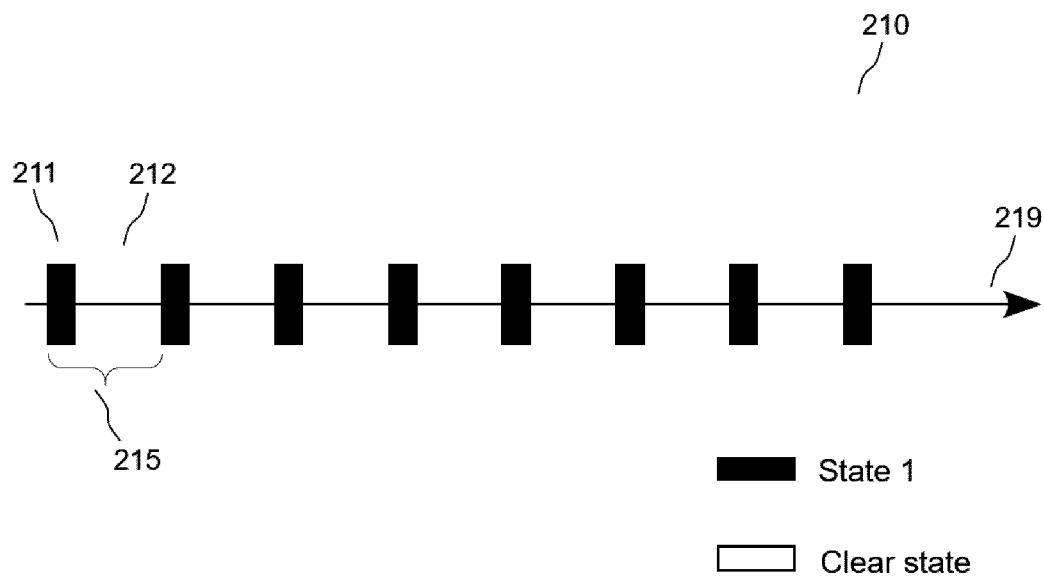
FIG. 2A shows a pre-determined time function in the form of a sequence of pulses of a first light, in accordance to various embodiments of the first aspect.

FIG. 2A shows a pre-determined time function 210 in the form of a sequence of a plurality of pulses of a first light, in accordance to various embodiments of the first aspect. On a time axis 219, the pulses 211 are shown as black boxes, and the first pulse duration, is the width of the black box on the time axis. Each pulse 211 may be followed by a clear state 212, wherein the clear state as a duration between two consecutive pulses. The pair formed by a single pulse 211 and the following clear state 212 may form a pulse pair. The pre-determined time function includes a plurality of pulse pairs, for example as a periodic function.

In various embodiments according to the first aspect, the pre-determined time function may include a pulse alternation between a pulse of the first light and a pulse of the second light.

Figure 2B:
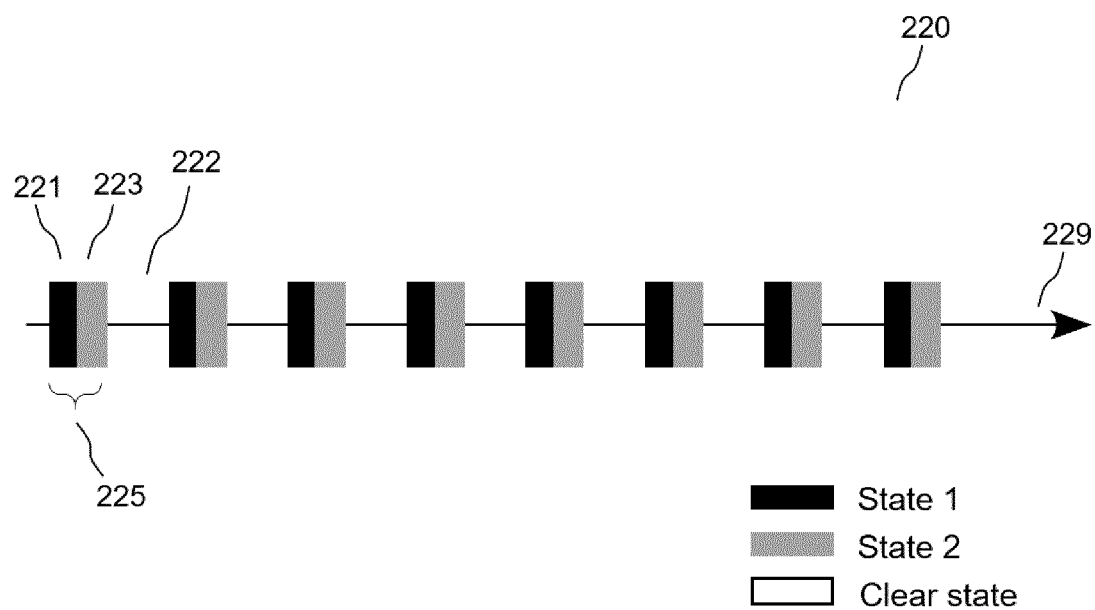
FIG. 2B shows a pre-determined time function in the form of a pulse alternation between a pulse of the first light and a pulse of the second light, in accordance to various embodiments of the first aspect.

FIG. 2B shows a pre-determined time function 220 in the form of a sequence of a plurality of pulses of a first light, further including a pulse of a second light in between two pulses of the first light, in accordance to various embodiments of the first aspect. On a time axis 229, the pulses 221 of first light are shown as black boxes, and first pulse duration, is the width of the black box on the time axis 229. A pulse 223 of a second light is shown as a grey box between consecutive pulses of the first light, with a respective pulse with or duration. The pre-determined time function may include the alternation of pulses of the first light and the second light. Each pulse 221 may be followed by a pulse 223, and each pulse 223 may be followed by a clear state 222. The set formed by a pulse 221 of the first light, a pulse 223 of the second light, and optionally the clear state 222 form a pulse set 225. The pre-determined time function may include a plurality of pulse sets, for example as a periodic function.

In various embodiments according to the first aspect, the pulse alternation may further include an interval between consecutive pulses of the first light and the second light.

Figure 2C:
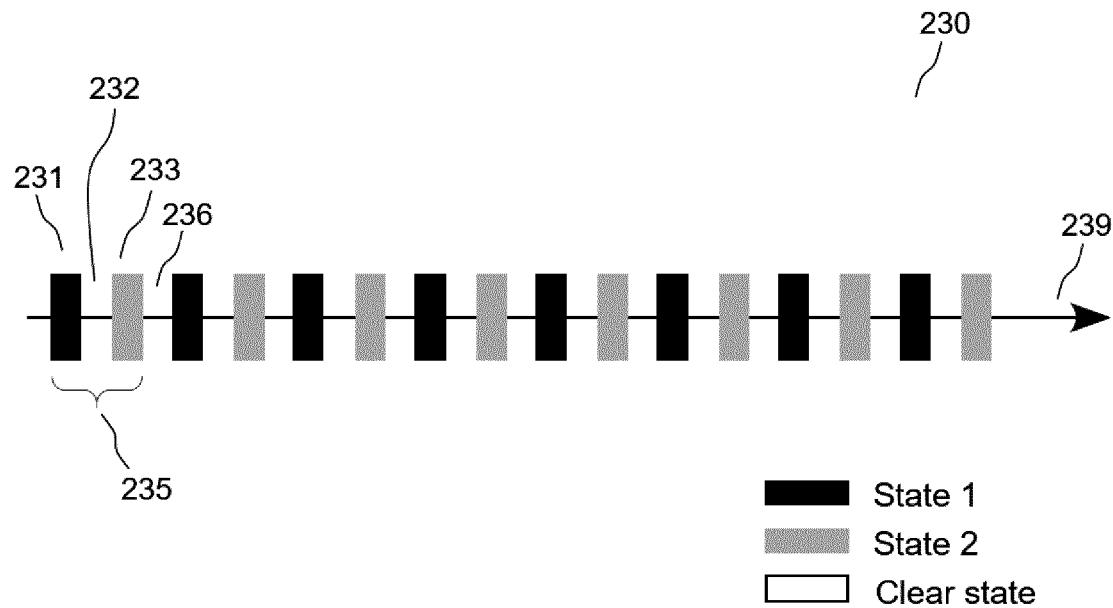
FIG. 2C shows a pre-determined time function in the form of a pulse alternation between a pulse of the first light and a pulse of the second light, in accordance to various embodiments of the first aspect, wherein the pulse alternation includes an interval between consecutive pulses of the first light and the second light.

FIG. 2C shows a pre-determined time function 230 in the form of a pulse alternation between a pulse of the first light and a pulse of the second light, in accordance to various embodiments of the first aspect, wherein the pulse alternation includes an interval between consecutive pulses of the first light and the second light. On a time axis 239, the pulses 231 of first light are shown as black boxes, and the first pulse duration is represented by the width of the black box on the time axis 239. A pulse 233 of a second light is shown as a grey box between consecutive pulses of the first light, with a respective pulse with or duration. The pre-determined time function may include the alternation of pulses of the first light and the second light. Each pulse 231 may be followed by a first clear state 232, which may be followed by a pulse 233 of second light, and each pulse 233 may be followed by a second clear state 236. The duration of the first clear state 232 and the duration of the second clear state 236 may be identical. The set formed by a pulse 231 of the first light, a first clear state 232, and a pulse 233 of the second light, and optionally the second clear state 236 form a pulse set 235. The pre-determined time function may include a plurality of pulse sets, for example as a periodic function.

In various embodiments according to the first aspect, the pre-determined time function may include a plurality of packets, wherein each packet of the plurality of packets may be followed by a packet interval. Each packet may include the pulse alternation. The pulse alternation may be repeated two or more times. It is well documented that neurons are more sensitive to a stimulation delivered in packets compared to 'simple' repetitive stimulation by alternative pulse. A good example of this is transcranial magnetic stimulation when delivered in packets (bursts) acts much faster than delivered in a standard repetitive meaner (similar results achieved in 3 minutes vs. ~30 minutes—in the article of Blumberger, D. M. et al., Lancet 2018, Vol. 391, "Effectiveness of theta burst versus high frequency repetitive transcranial magnetic stimulation in patients with depression (THREE-D): a randomised non-inferiority trial"). Although the intermittent theta burst stimulation (iTBS) mentioned in said Blumberger, D. M. paper targets brain neurons, it is conceivable that similar mechanisms may be present in the neurons in the eye, specifically the iPRGs as mentioned in present patent and therefore the light stimulation delivered in bursts (packets) may achieve similar results in a shorter time.

Figure 2D:
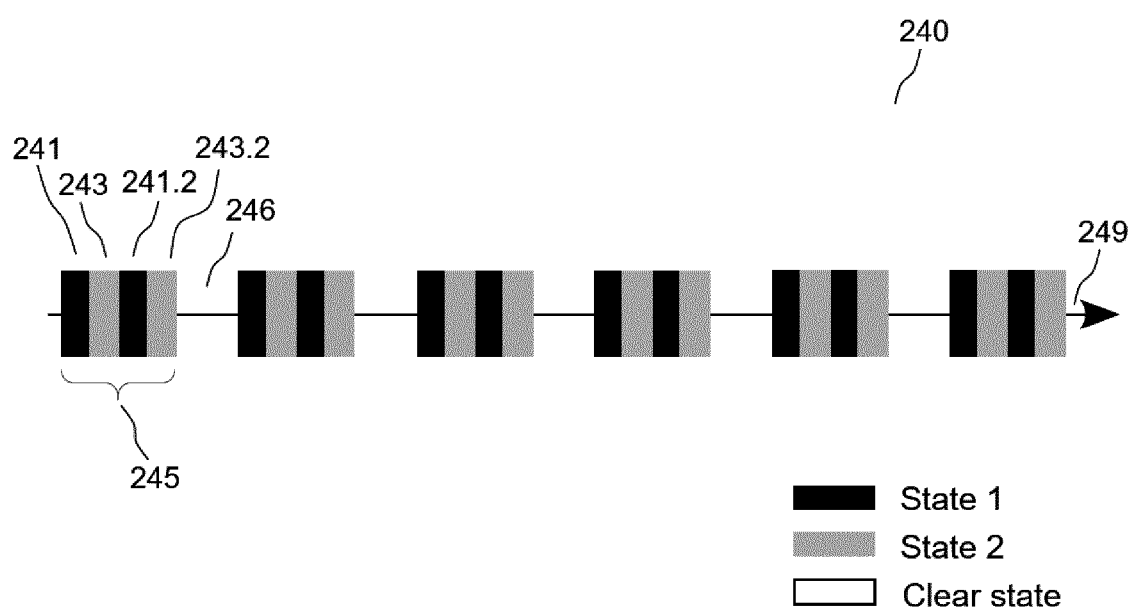
FIG. 2D shows a pre-determined time function including a plurality of packets followed by a packet interval, in accordance to various embodiments of the first aspect. Each packet may include the pulse alternation.

FIG. 2D shows a pre-determined time function 240 including a plurality of packets followed by packet intervals, in accordance to various embodiments of the first aspect. Each packet may include the pulse alternation. For example, a pulse alternation may include a pair of a pulse 241 of the first light followed by a pulse 243 of the second light, wherein the pair is repeated two (e.g. with further pulse 241.2 of the first light and 243.2 of the second light) or more times, thus forming the alternation included in the packet 245. Each of the packets 245 may be followed by a packet interval 246, which may be a clear state. The time duration of each packet is in the range of 1-5 seconds, preferably 2 seconds. The duration of each packet interval is in the range of 5-20 seconds, preferably 8 seconds. The study on brain neurons shows the typical stimulation delivered in packets follow a pattern where 1 packet lasts about 2 seconds and the duration between the packets is about 8 seconds. This pattern is very effective for the brain neurons but similar pattern is to be expected effective also in the eye neurons.

The activation of ipRGCs may be manipulated by changes in light source color, for example delivering bright flashes of light alternating between ipRGC-selective spectrum (blue light) and ipRGC-nonselective (red, yellow, etc. . . . ) colors at a specific frequency or in bursts. Such illumination system may use LEDs as a light source, for example interchanging the emitted light in front of a source of white light. An exemplary application of this setup may be an eyewear, which may, for example be normally worn during the day, and which may be switched between a "normal mode" to an "active treatment mode". This embodiment provides a good deal of flexibility and can be used patients with both moderate and severe myopia.

In various embodiments according to the first aspect, the illumination system may further include a button, for example an electrical button. The button may be configured to switch the light source between at least an active mode and an inactive mode. In the active mode, the light source may emit pulses of light with the pre-determined time function. In the inactive mode the light source does not emit light.

In a second aspect, an eyewear is provided. The eyewear may include a spectacle frame and the illumination system according to various embodiments according to the first aspect.

In various embodiments according to the second aspect, the eyewear may further include at least a pair of spectacle lenses mounted on the spectacle frame.

In various embodiments according to the second aspect, the light source of the illumination system may be mounted on the spectacle frame or on the spectacle lens.

Figure 3:
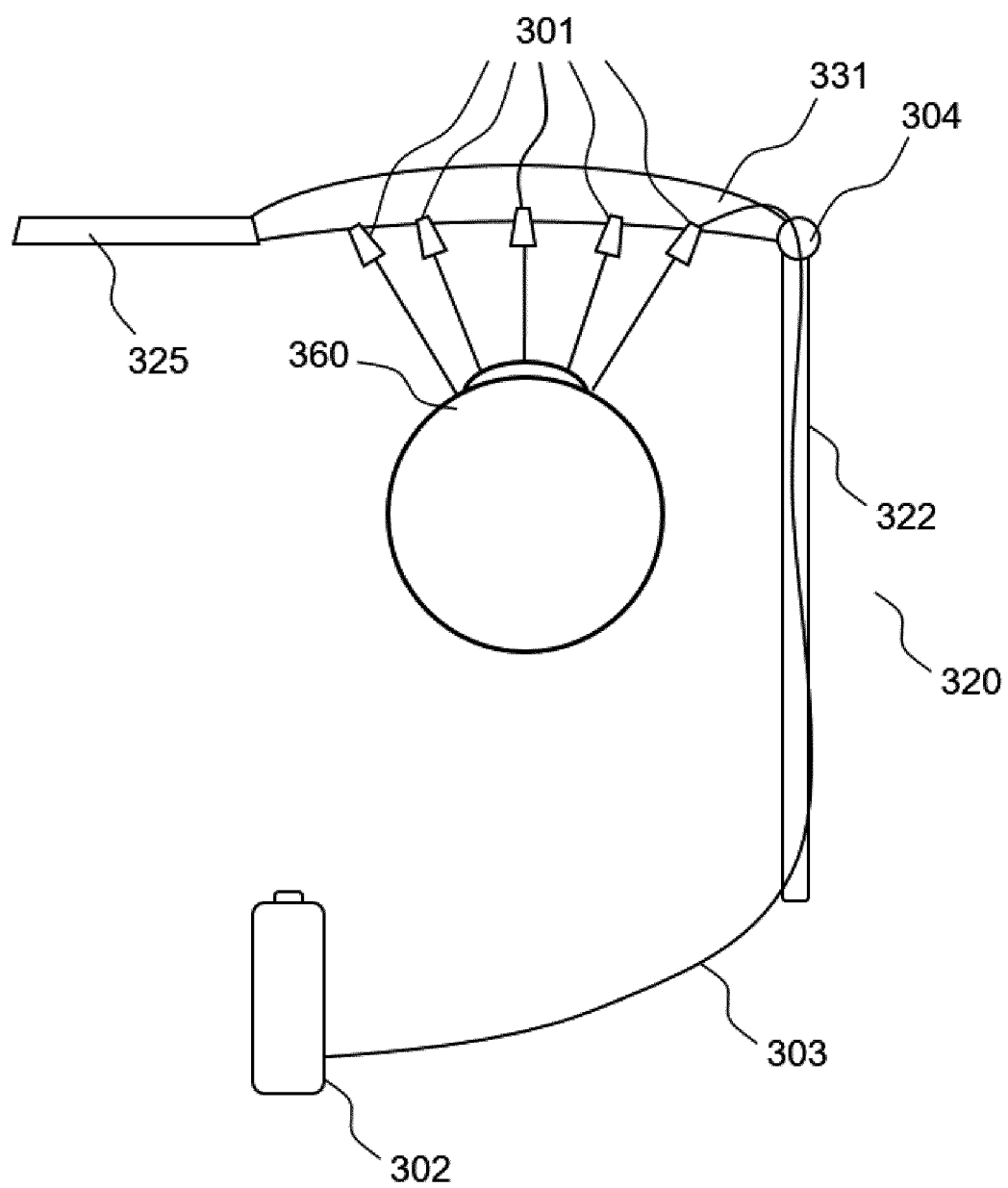
FIG. 3 is a schematic illustration of an eyewear, in accordance to various embodiments of the second aspect, including a spectacle frame and the illumination system according to various embodiments according to the first aspect, wherein the light source of the illumination system may be mounted on the spectacle frame or on the spectacle lens.

FIG. 3 shows an illumination system according to various embodiments according to the first aspect, wherein the light source 301 of the illumination system may be mounted on a spectacle frame 320 or on the spectacle lens 331. FIG. 3 also shows a schematic illustration of an eyewear, in accordance to various embodiments of the second aspect, including a spectacle frame 320 and the illumination system. In FIG. 3 the illumination system is shown included in the eyewear for illustration purposes. However, the system may also be provided independently from an eyewear.

As illustrated by means of example, the eyewear may include a spectacle frame 320. Only one side of the eyewear and of the spectacle frame is shown for ease of reference. The spectacle frame may be symmetric, thus the not shown side may be minor symmetric to the shown side. Similarly, the eyewear may be symmetric, thus the not shown side may be minor symmetric to the shown side. The spectacle frame may include a bridge 325 for connecting the lenses and/or rims for lenses, and my further include a pair of earpieces (only 322 shown).

The illumination system may include a light source 301, which light source may include one or more light emitters, e.g. one or more light emitting diodes. As illustrated by means of example, the light source may be mounted on the lens 331, or alternatively or in addition on the spectacle frame 320, such that when they emit light, light is emitted in the direction of an wearer's eye 360. Said direction may be, for example, to the side having the ear pieces. For example, the light source 301 may include LED(s) arranged such that light is emitted by the LEDs onto a wearer's eye 360 direction. For example directly, without any other optical means in the light path between the LEDs and a position for a wearer's eye.

The illumination system may further include a power source 302, which may be electrically couple to the light source 301, for example via a conductor 303. An example for a conductor is a pair of conductor wires. The system may further include a button. The system may also include a sensor 304.

FIG. 3 shows that the illumination system is coupled to the eyewear. For example, the conductor 303 may be coupleable or otherwise integrated into the spectacle frame 320, for example the ear piece 302.

In various embodiments according to the second aspect, the light source of the illumination system may be configured to emit light in a direction to a wearer's eye, when the wearer is wearing the pair of spectacles.

In various embodiments according to the second aspect, the light source of the illumination system and the spectacle lens may be configured so that light emitted by the light source of the illumination system is at least partially reflected by the spectacle lens, in a direction to a wearer's eye, when the wearer is wearing the pair of spectacles.

Figure 4:
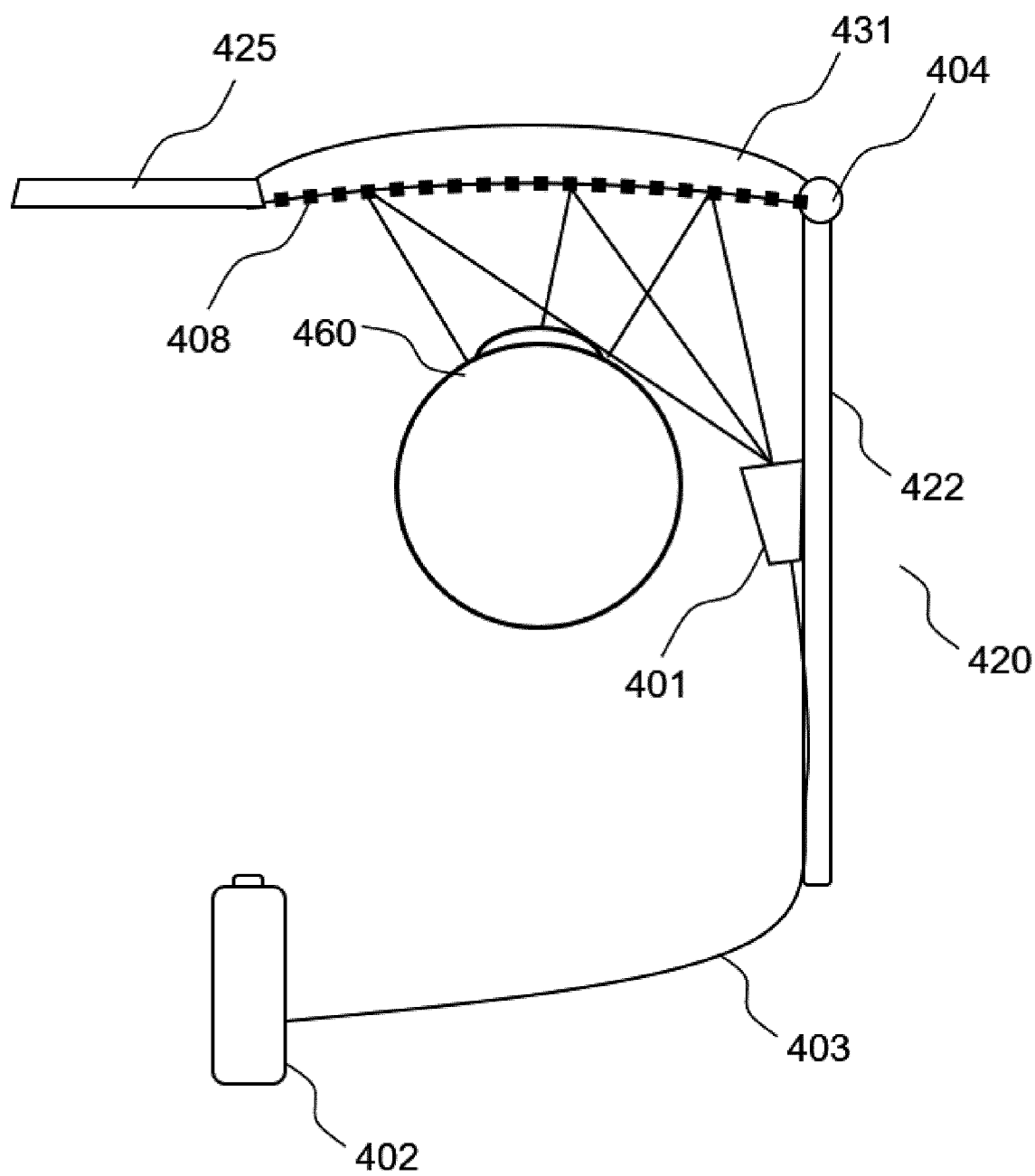
FIG. 4 is a schematic illustration of an eyewear, in accordance to various embodiments of the second aspect, including a spectacle frame and the illumination system according to various embodiments according to the first aspect, configured so that light emitted by the light source of the illumination system is at least partially reflected by the spectacle lens, in a direction to a wearer's eye.

FIG. 4 is a schematic illustration of an eyewear, in accordance to various embodiments of the second aspect, including a spectacle frame and the illumination system according to various embodiments according to the first aspect, configured so that light emitted by the light source of the illumination system is at least partially reflected by the spectacle lens, in a direction to a wearer's eye. In FIG. 4 the illumination system is shown included in the eyewear for illustration purposes. However, in some embodiments, the illumination system may also be provided independently from an eyewear.

As illustrated by means of example, the eyewear may include a spectacle frame 420. Only one side of the eyewear and of the spectacle frame is shown for ease of reference. The spectacle frame may be symmetric, thus the not shown side may be minor symmetric to the shown side. The eyewear may be symmetric, thus the not shown side may be mirror symmetric to the shown side. The spectacle frame may include a bridge 425 for connecting the lenses and/or rims for lenses, and my further include a pair of earpieces (only 422 shown).

The illumination system may include a light source 401, which light source may include one or more light emitters, e.g. one or more light emitting diodes. As illustrated by means of example, the light source may be coupleable to the spectacle frame 420, for example mounted on the ear piece 422. The illumination system may include a reflection means 408, for example a spectacle lens 431 may include the reflection means, and thus be configured so that light emitted by the light source 401 is at least partially reflected by the spectacle lens 431, in a direction to a wearer's eye 460, when the wearer is wearing the eyewear, for example the spectacles.

In various embodiments according to the second aspect, the spectacle lens may be configured to be at least partially reflective in the first range of wavelengths. In one example, the lens may include a reflective layer, for example be coated with the reflective layer, wherein the reflective layer is configured to reflect light within the wavelength range of the first light emitted by the light source 401. In another example, the reflective element in the lens can be an holographic mirror. In various embodiments according to the second aspect, the spectacle lens may be further configured to be at least partially reflective in the second range of wavelengths.

The illumination system may further include a power source 402, which may be electrically couple to the light source 401, for example via a conductor 403. An example of a conductor 403 is a pair of conductor wires. The system may further include a button. The system may also include a sensor 404.

FIG. 4 shows that the illumination system may be coupleable to the eyewear. For example, the conductor 403 may be coupleable or otherwise integrated into the spectacle frame 420, for example the ear piece 402.

In a third aspect, an optical filter system, adapted for a spectacle lens, is provided. The optical filter system may include a band-cut filter. The band-cut filter may be configured to be in a band-cut filter state under a low light condition and not in the band-cut filter state under a high light condition. In the band-cut filter state, the filter may include a band-cut filter spectrum including a cut band. According to various embodiments, the low light condition may be a low blue light condition, which low blue light condition is when an incident light intensity, within the range of wavelength of the blue light, is equal to or lower than a light intensity threshold. According to various embodiments, the high light condition may be a high blue light condition, which high blue light condition is when the incident light intensity, within the range of wavelength of the blue light, is higher than the light intensity threshold.

According to various embodiments, the band-cut filter and/or the band-pass filter may include at least one cell comprising a transparent liquid crystal formulation between two transparent supports, at least one of the transparent supports comprises a transparent electrode.

According to one embodiment, the transparent liquid crystal formulation placed between the two transparent supports may be in a blue phase organization with a size of the cubic mesh in the predetermined range of wavelengths to be filtered, for example, in the cut band. The blue phase organisation may be stabilised in the useful range of temperature by known methods. The cubic mesh of the blue phase may be controlled by the electrical field between the transparent supports using the at least one transparent electrode.

According to another embodiment, the transparent material may be placed between the two transparent supports and may comprise at least a liquid crystal matrix whose orientation changes upon application of an electrical field and at least one dichroic dye having its absorption range in the predetermined range of wavelengths to be filtered, for example, in the cut band. The dichroic dyes may be chosen to have an absorption spectrum in the area of desired wavelengths. Once incorporated in the liquid crystal matrix they provide an absorbing effect. The absorption effect may be controlled by the electrical field between the transparent supports using the at least one transparent electrode.

In various embodiments according to the third aspect, the cut band may encompass the wavelengths of 450 nm to 495 nm.

According to various embodiments, a filter's cut band, for example the cut band of the band-cut filter, may refer to a wavelength band in which the filter has a decreased transmittance. E.g. less than 50% transmittance, in relation to a baseline which may be, e.g., higher than 95% transmittance. The wavelength band may have a bandwidth defined as Full Width at Half Minimum (FWHMi) of the transmittance. The wavelength band may include a center wavelength, which is the midpoint of the FWHMi. The FWHMi may be selected from 10 nm to 150 nm, for example it may be less than 100 nm.

Figure 5A:
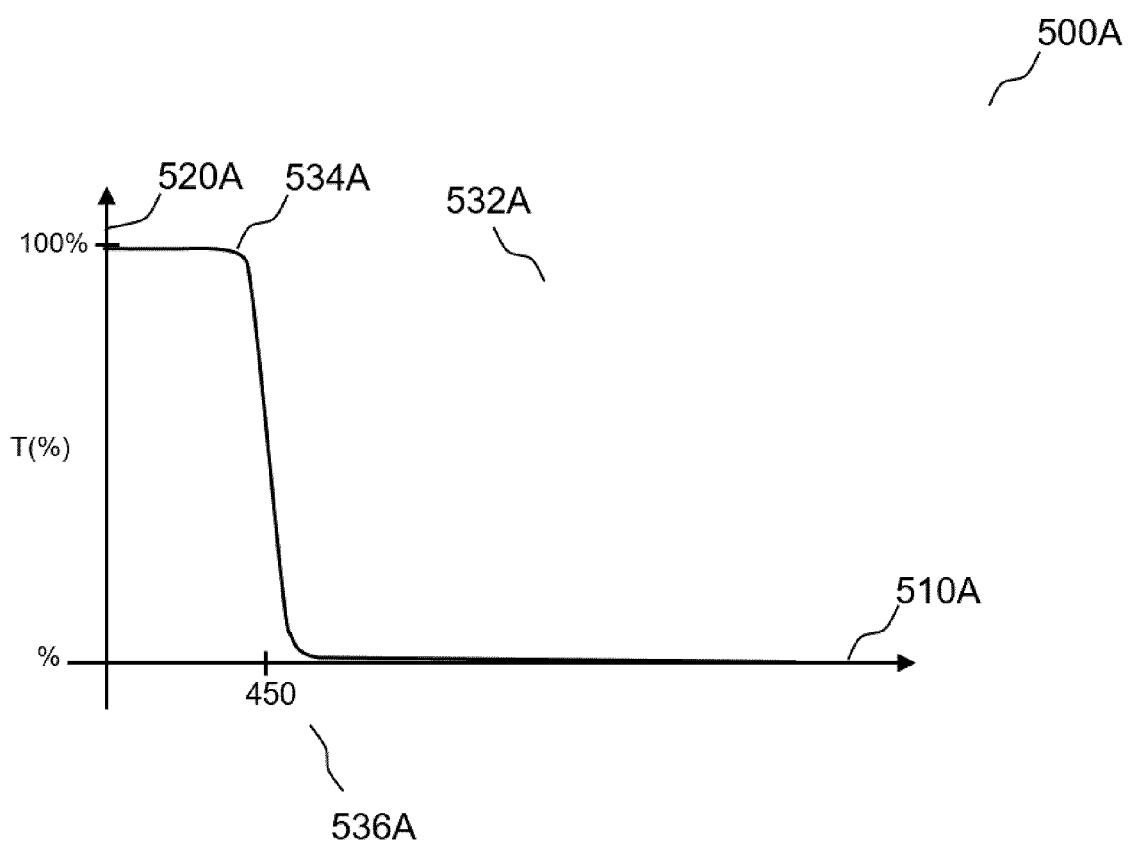
FIGS. 5A and 5B show exemplary transmission spectra of a band-cut filters in the band-cut state, in accordance to various embodiments of the third aspect.

FIG. 5A shows an exemplary transmission spectrum of a band-cut filter in the band-cut state, in accordance to various embodiments of the third aspect. It is shown, in a graphic 500A with a vertical axis 520A schematically representing the transmittance ranging from 0% (totally blocking) to 100% (totally transparent) as function of the wavelength shown in the horizontal axis 510A, in nanometers (nm), of a transmittance spectrum 530A. The spectrum 530A has cut-band 532A between a wavelength range with a lower wavelength of the FWHMi of exemplary 450 nm and an upper wavelength of the FWHMi longer than 495 nm, for example longer than 720 nm, for example in the near infra red or longer. The transmission base line 534A of the band-cut filter's spectrum may be naturally a few % points, e.g. 10% or less, below 100%.

Figure 5B:
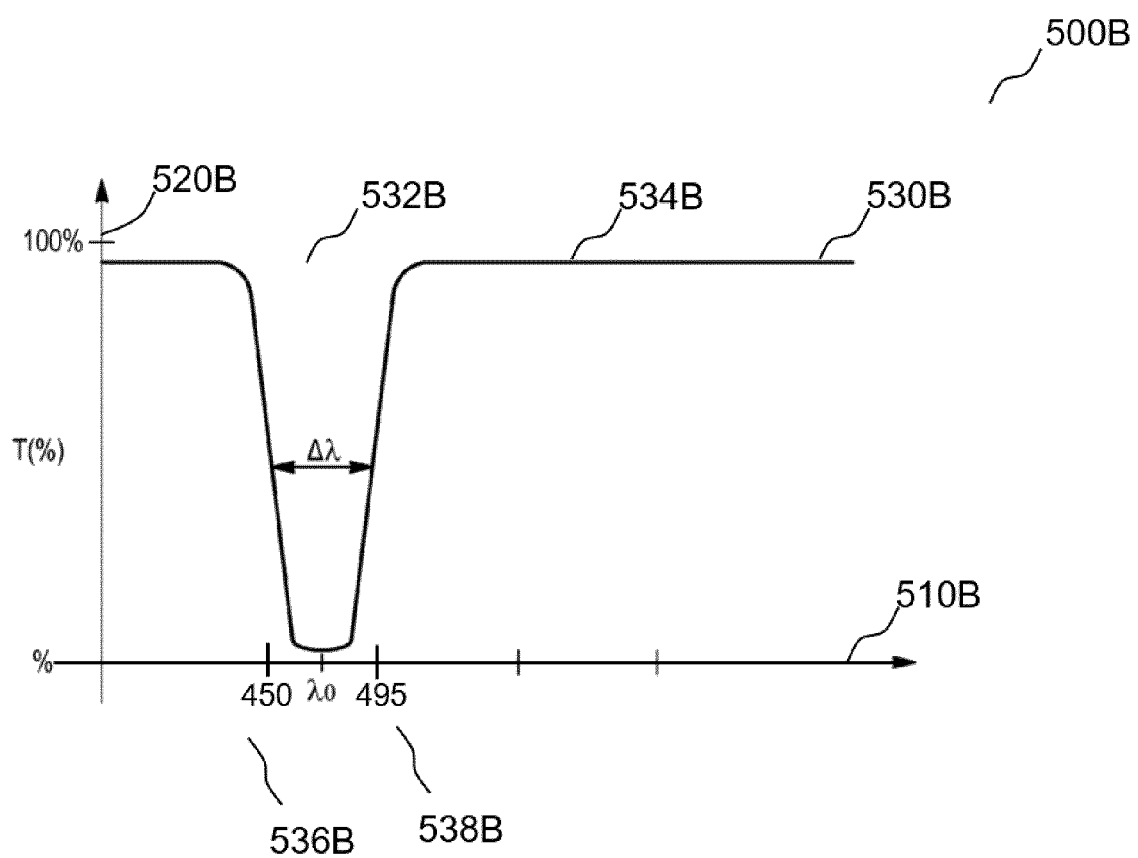

FIG. 5B shows an exemplary transmission spectrum of a band-cut filter in the band-cut state, in accordance to various embodiments of the third aspect. It is shown, in a graphic 500B with a vertical axis 520B schematically representing the transmittance ranging from 0% (totally blocking) to 100% (totally transparent) as function of the wavelength shown in the horizontal axis 510B, in nanometers (nm), of a transmittance spectrum 530B. The spectrum 530B has cut-band 532B with a center wavelength (absorption center) centered at $\lambda_0$ between a wavelength range with a lower wavelength of the FWHMi of exemplary 450 nm and an upper wavelength of the FWHMi of exemplary 495 nm. The transmission base line 534B of the band-cut filter's spectrum may be naturally a few % points, e.g. 10% or less, below 100%.

In various embodiments according to the third aspect, the optical filter may further include a band-pass filter. The band-pass filter may be configured to be in a band-pass filter state under the high blue light condition and not in the band-pass filter state under the low blue light condition. In the band-pass filter state, the filter may include a band-pass filter spectrum including a pass band.

According to various embodiment, the band pass filter may be provided as described above, wherein a liquid crystal formulation, for example in a blue absorbing phase, is placed between the two transparent supports. The liquid crystal formulation may include further dyes which absorb in the range out of the pass-band and are not electronically active. Alternatively or in addition, the filter may include a non-electronically active filter with a fixed pass band. Thus, the absorption effect (e.g. blue absorbing phase) of the liquid crystal may be controlled by the electrical field between the transparent supports using the at least one transparent electrode. When an electrical field is applied, the filter changes from opaque to transparent in the pass band.

Without wishing to be bound by theory it is believed that that magnitude of sensory cell's response to a particular stimulus is stronger after stimulus deprivation. Thus, it is believed that due to light deprivation in the band-cut spectrum (for example via a blue-cut filter) in low blue light conditions (for example indoors) combined with the band-cut filter not being in the band-cut filter state under high blue light conditions, a strong stimulus of the ipRGC's response may be obtained. Accordingly, it is believed that a stronger stimulus of the ipRGC's response may be obtained, when, in addition to the light deprivation under low blue light condition, a light enhancement in the band-cut spectrum (e.g. via a blue-pass filter) is provided under high blue-light conditions (for example outdoors). The light enhancement in the band-cut spectrum may be obtained, for example, with the band-pass filter, which spectrum may overlap the band-cut spectrum.

In various embodiments according to the third aspect, the pass band encompasses the wavelengths of 450 nm to 495 nm, for example, it may encompass the wavelengths of 460 nm to 484 nm.

According to various embodiments, a filter's pass band, for example the pass band of the band-pass filter, may refer to a wavelength band in which the filter has an increased transmittance. E.g. more than 50% transmittance, in relation to a baseline which may be e.g. lower than 5% transmittance. The wavelength band may have a bandwidth defined as FWHM of the transmittance band. The wavelength band may include a center wavelength, which is the midpoint of the FWHM.

Figure 6A:
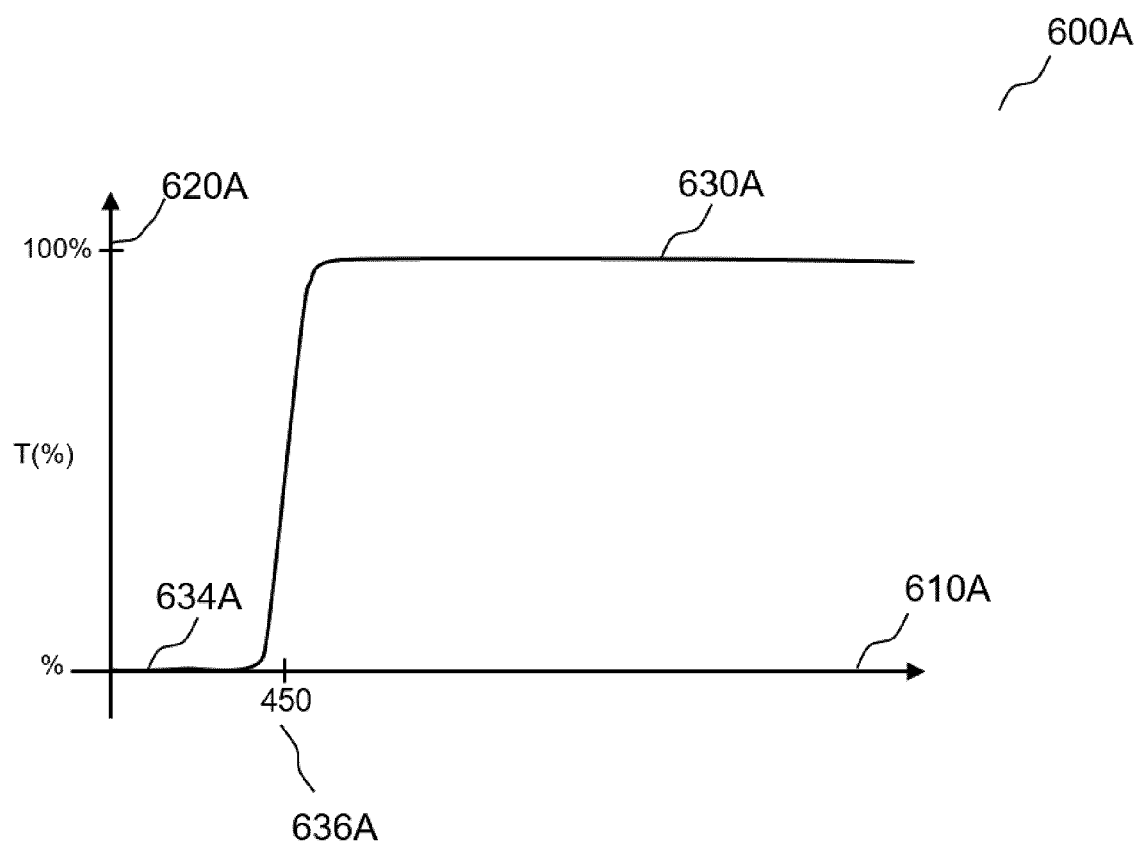
FIGS. 6A and 6B show exemplary transmission spectra of a band-pass filters in the band-pass state, in accordance to various embodiments of the third aspect.

FIG. 6A shows an exemplary transmission spectrum of a band-pass filter in the band-pass state, in accordance to various embodiments of the third aspect. It is shown, in a graphic 600A with a vertical axis 620A schematically representing the transmittance ranging from 0% (totally blocking) to 100% (totally transparent) as function of the wavelength shown in the horizontal axis 610A, in nanometers (nm), of a transmittance spectrum 630A. The spectrum 630A has a pass-band 635A between a wavelength range with a lower wavelength of exemplary 450 nm of the FWHM and an upper wavelength of the FWHM longer than 495 nm, for example longer than 720 nm, for example in the near infra red or longer. The base line 634B of the band-pass filter's spectrum may be lower than 5%, for example essentially 0%.

Figure 6B:
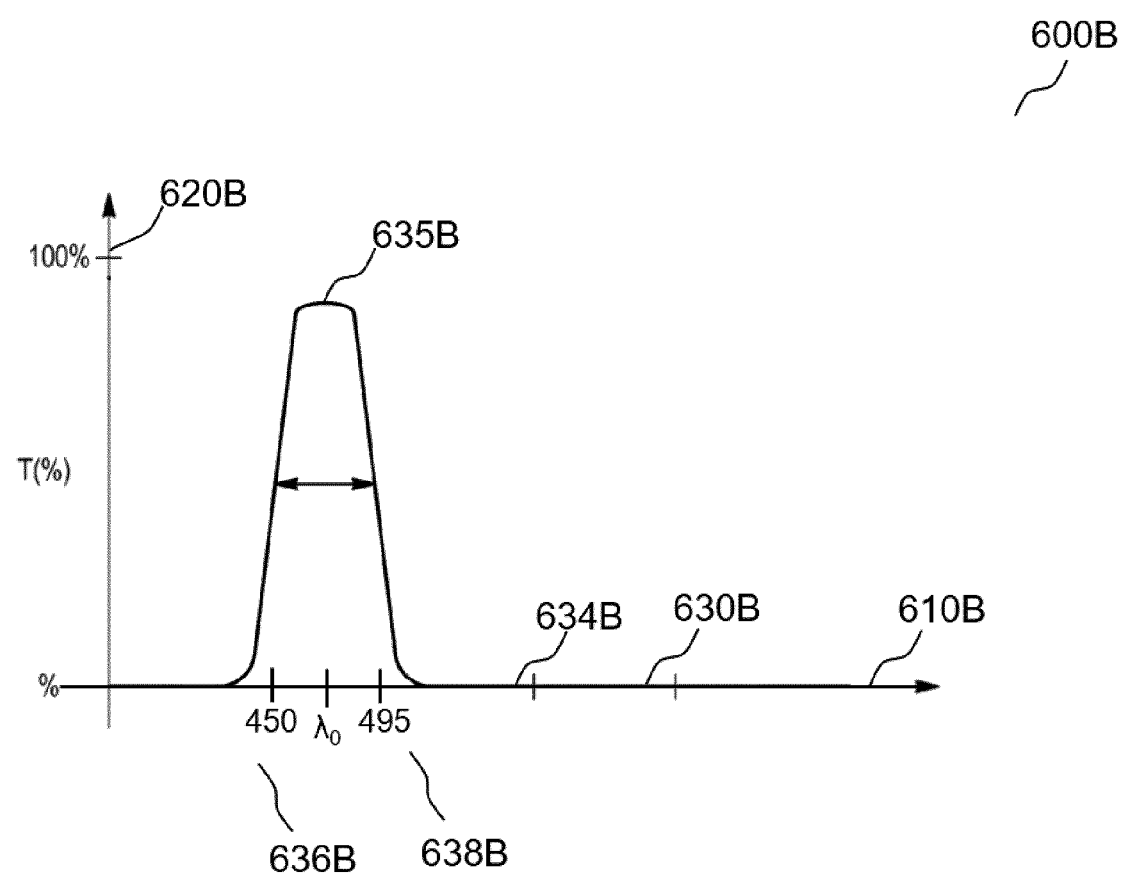

FIG. 6B shows an exemplary transmission spectrum of a band-pass filter in the band-pass state, in accordance to various embodiments of the third aspect. It is shown, in a graphic 600B with a vertical axis 620B schematically representing the transmittance ranging from 0% (totally blocking) to 100% (totally transparent) as function of the wavelength shown in the horizontal axis 610B, in nanometers (nm), of a transmittance spectrum 630B. The spectrum 630B has a pass-band 635B centered at $\lambda_0$ between a wavelength range with a lower wavelength of exemplary 450 nm of the FWHM and an upper wavelength of exemplary 495 nm of the FWHM. The base line 634B of the band-pass filter's spectrum may be lower than 5%, for example essentially 0%.

In various embodiments according to the third aspect, the pass band and the cut band at least partially overlap.

In various embodiments according to the third aspect, the wavelength range of the incident light intensity may at least partially overlap with the wavelength range of: the cut band, or of the pass band, or of the cut band and the pass band.

In various embodiments according to the third aspect, the optical filter system may further include a sensor configured to detect the incident light intensity.

In various embodiments according to the third aspect, the optical filter system may further include a circuit electrically coupled to the sensor. The circuit may be coupled to the band-cut filter. The circuit may further be configured to set the band-cut filter in or out of the band-cut filter state, for example in accordance with the light intensity threshold. Alternatively or in addition, the circuit may be coupled to the band-pass filter and may further be configured to set the band-pass filter in or out of the band-pass state in accordance with the light intensity threshold. The circuit configured to set the band-pass filter may be a separate circuit or part of a common circuit in common with the circuit configured to configure the state of the band-cut filter.

In various embodiments according to the third aspect, the light intensity threshold may be in the range from 0.33 cd/m$^2$ to 44.4 cd/m$^2$, for example in the range from 5 cd/m$^2$ to 20 cd/m$^2$. For example, if the threshold is set to 0.35 cd/m$^2$ and the sensor measures a light intensity equal to or lower than 0.35 cd/m$^2$, then the band-cut filter is configured to be in the band-cut state, and when the sensor measure a light intensity higher than 0.35 cd/m$^2$, then the band-cut filter is configured to not be in the band-cut state.

In various embodiments according to the third aspect, the light intensity threshold may be adjustable. An adjustability of the light intensity threshold may be implemented in the form of a circuit, which may be, e.g. tuned to set the desired threshold. The adjustability may be advantageous as the threshold may be adjusted based to personalize the threshold to a wearer.

In a fourth aspect, a spectacle lens is provided according to various embodiments according to the third aspect.

In a fifth aspect, an eyewear is provided according to various embodiments according to the third aspect. The eyewear may include the optical filter system according to the third aspect.

In various embodiments according to the fifth aspect, the eyewear may further include a spectacle frame. The eyewear may further include the sensor from the optical system, alternatively or in addition, the eyewear may include a spectacle frame integrated sensor configured to detect the incident light intensity, wherein the spectacle frame integrated sensor is integrated into the spectacle frame.

Figure 7A:
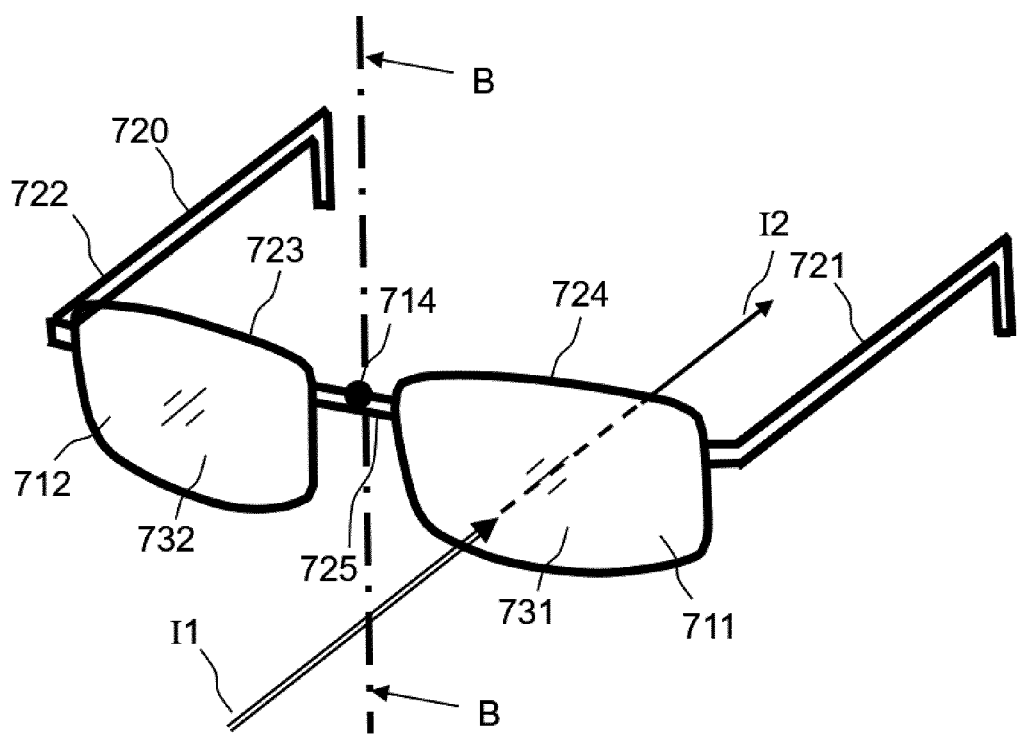
FIG. 7A is a schematic illustration of an eyewear, in accordance to various embodiments of the fifth aspect, including a spectacle frame and the optical filter system according to the third aspect.

FIG. 7A is a schematic illustration of an eyewear, in accordance to various embodiments of the fifth aspect, including a spectacle frame and the optical filter system according to the third aspect. FIG. 7A shows an example of an optical filter system 711 coupled to a spectacle frame 720 of an eyewear. The optical filter system 711 may be integral part of a lens 731 or may be coupleable to a lens 731. The spectacle frame 720 may include a bridge 725 connecting to lenses 731 and 732 and/or rims for lenses 723 and 724, and my further include a pair of earpieces 721 and 722. The eyewear may include a second optical filter system 712, which may be integral part of the lens 732 or may be coupleable to the lens 732.

Figure 7B:
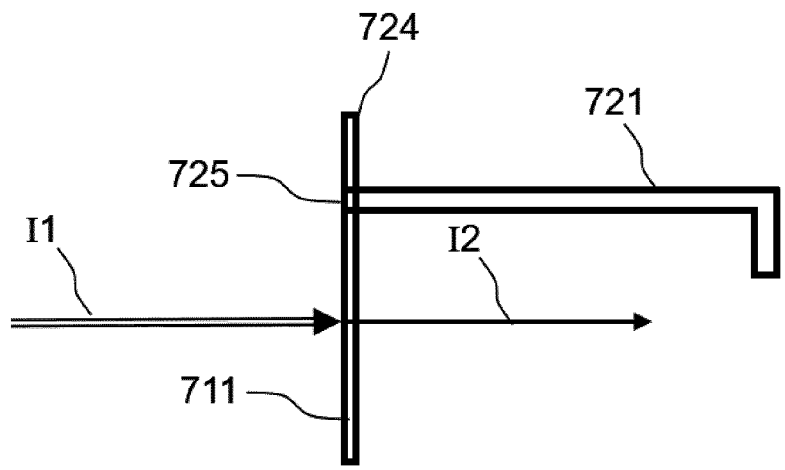
FIG. 7B is the cross sectional view B-B of FIG. 7A.

FIG. 1B is the cross sectional view B-B of FIG. 7A. As can be seen in FIG. 7A and FIG. 7B, at a pre-determined position, the light intensity may be I2, which may be the outcome of the light I1 filtered by the optical filter system 711. Incident light I1 may be, as illustrated by means of example, light that is crossing lenses 731 or rims for lenses 724.

Figure 8:
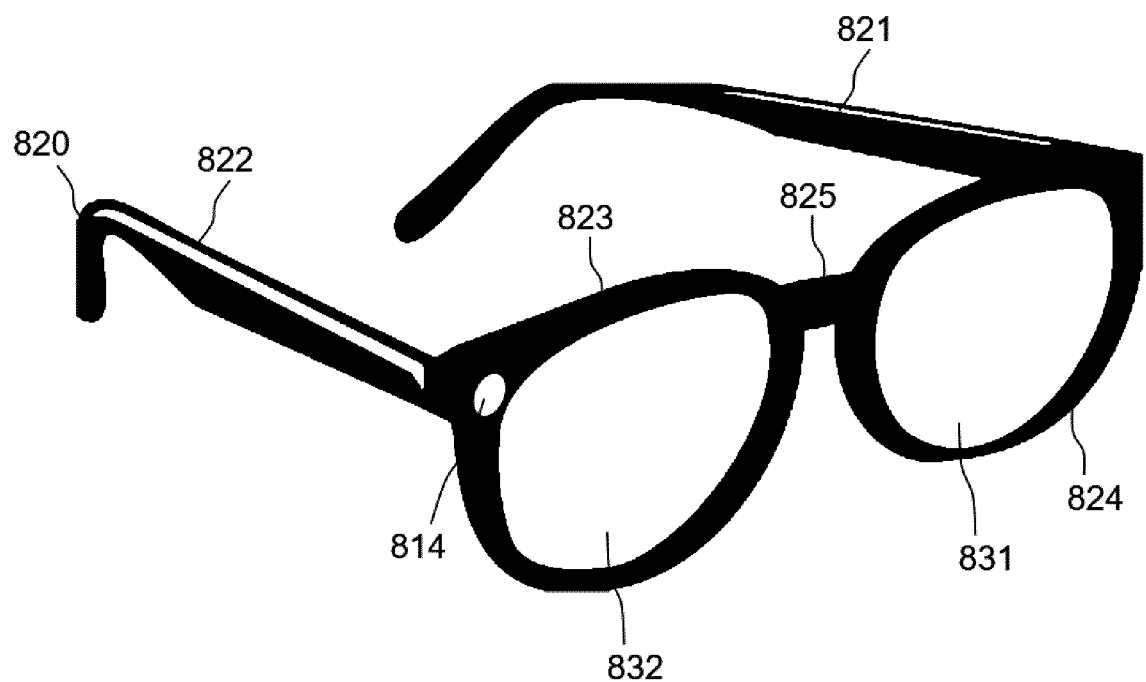
FIG. 8 is a schematic illustration of an eyewear including a sensor.

FIG. 8 shows an eyewear in accordance to various embodiments. The eyewear may include a spectacle frame 820, and a bridge 825 connecting the rims 823 and 824 for lenses 832 and 824 respectively. The spectacle frame 820 may further include earpieces 821 and 822. The spectacle frame may include an integrated sensor 814. The spectacle frame may include a receptacle, e.g. a cavity, configured for receiving a sensor for the illumination system and/or the optical filter system, alternatively or in addition the spectacle frame may include a sensor, which is formed as integral part of the spectacle frame and which is coupleable, e.g. electrically coupleable, with a remaining part of the illumination system and/or the optical filter system. Thus, it is possible to provide an eyewear wherein the sensor is well integrated and does not substantially change the appearance of the eyewear.

Figure 9:
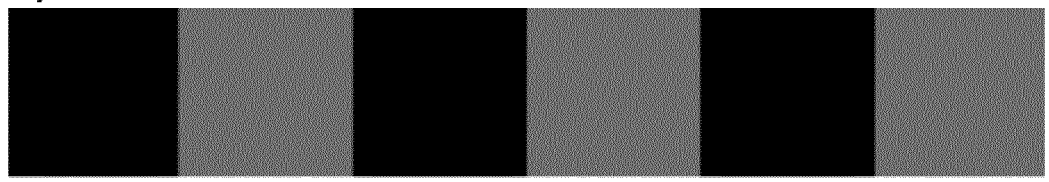
FIG. 9 shows examples of two sudden and one gradual changes between different states, of an illumination system or an optical filter system, according to various embodiments.
Figure 9:
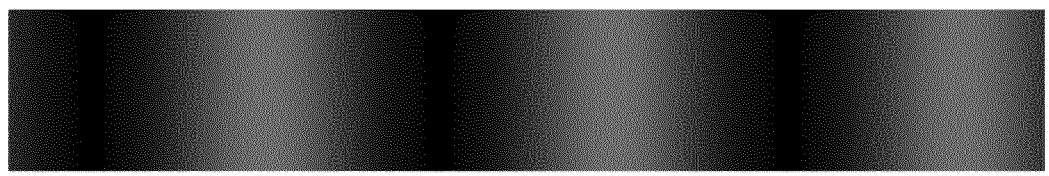
Figure 9:
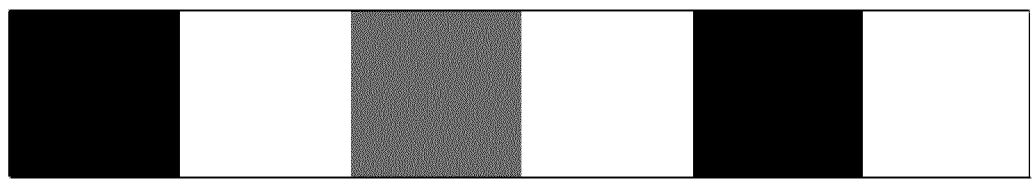

As previously described, the illumination system and the optical filter system may be configured to provide changes in light aimed at a wearer's eye position. For example, the illumination system may be configured to emit a sequence and/or alternation of light pulses, and the optical filter system may be configured to filter incident light. According to various embodiments, these changes may be sudden or gradual. FIG. 9 shows examples of two sudden and one gradual changes according to various embodiments.

The pattern A) of FIG. 9 shows a sudden change between a state 1 and a state 2, for example, the illumination system may emit light of a first light (State 1) during a first period of time, e.g. the pulse of the first light, which illumination system may be configured to abruptly change to emit light of a second light (State 2) during a second period of time, e.g. the pulse of the second light, which sudden changes may occur between the first light and the second light, for example as an alternation as previously explained. In contrast to the pattern A), in pattern B) the change may be gradual, for example, for the illumination system, the first light would gradually fade while at the same time the second light would gradually brighten. The pulse duration, which could also be named as pulse width, could be determined for each light, for example as the FWHM of the light intensity over time for each light, e.g. for the first light and the second light. Pattern C) of FIG. 9 shows abrupt changes of the states, from a pulse of a first state to a clear state and a pulse of a second state followed by another clear state. The pulse duration may be selected for example from 0.02 seconds to 20 seconds, for example from 0.03 seconds to 10 seconds.

Similarly as explained above for the illumination system, the optical filter system may be configured to provide a similar pattern. For pattern A) of FIG. 9, the sudden change between a state 1 and a state 2, may be, for example that in state 1 the band-cut filter is in the active mode and the and band-pass filter is not be in the active mode. State 1 may change into state 2 abruptly, in which for example, the band-cut filter is not be in the active mode and the band-pass filter is in the active mode. In contrast to the pattern A), in pattern B) the change may be gradual, for example, for the optical system, the filters may activate and deactivate gradually, such that from state 1 to state 2, band-cut filter would gradually fade from the active mode into the not active mode, while the band-bass filter would gradually activate from the not active mode into the active mode. The reverse would occur from a gradual change from state 2 to state 1. The pulse duration, which could also be named as pulse width, could be determined for spectrum, for example as the FWHM of the transmittance signal over time for each spectrum, for example by measuring the transmittance for each filter measured separately. The pulse duration may be selected for example from 0.02 seconds to 20 seconds, for example from 0.03 seconds to 10 seconds.

Pattern C) of FIG. 9 shows abrupt changes of the states, wherein a clear state follows after each state 1 and state 2.

In various embodiments according to the third aspect, the band-cut filter may include a band-cut filter passive zone and a band-cut filter active zone. The band-cut filter active zone may be provided at a periphery of the band-cut filter passive zone.

In various embodiments according to the third aspect, the band-pass filter includes a band-pass filter passive zone and a band-pass filter active zone. The band-pass filter active zone may be provided at a periphery of the band-pass filter passive zone.

Figure 10A:
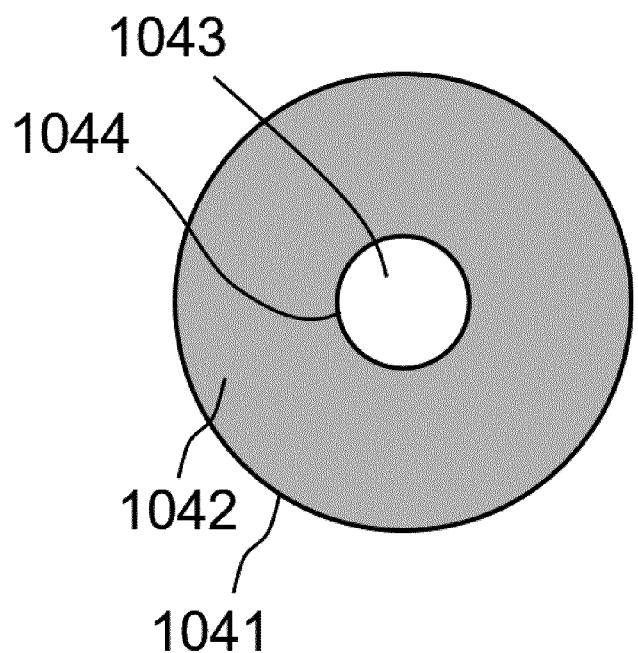
FIG. 10A and FIG. 10B show a further development of the aspects of the present invention, wherein, the optical filter system 1041 and 1051 may include a distribution by zones.
Figure 10B:
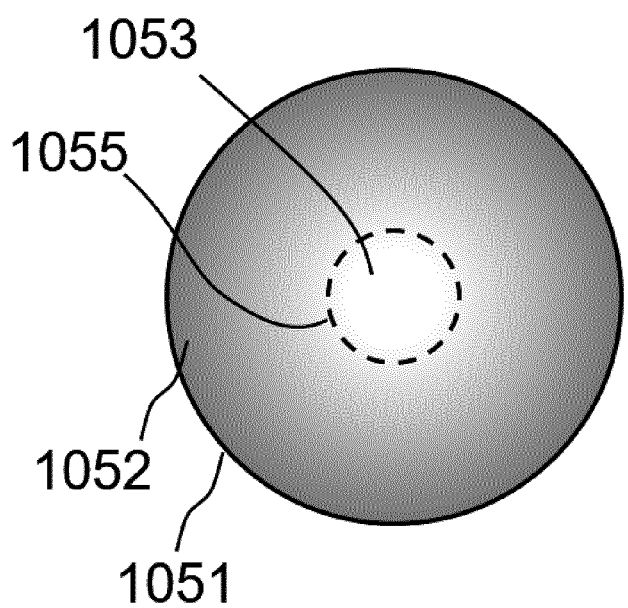

FIG. 10A and FIG. 10B show a further development of the aspects of the present invention, wherein, the optical filter system 1041 and 1051 may include a distribution by zones, for example, the optical filter system may have a central zone 1043 or 1053, in which the optical filter system has a constant state, for example a clear state, and an outer zone 1042 or 1052, in which the optical filter system may be active, for example in which outer zone the band-cut filter and/or band-pass filter may each independently change between the active mode and the not active mode.

It is believed that the distribution of the ipRGCs is not homogenous, and may be denser in the periphery of an eye. Therefore, it may be beneficial having the 'color-changing zone' in the periphery of the visual field. Such solution would also have lesser impact on color processing in the central visual field. The transition between the active and passive zones may be sharp (FIG. 10A) or follow a particular pattern, e.g. can be smooth (FIG. 10B). Given the expected impact on aesthetics of this embodiment, it may be prescribed and accepted more by patients with severe myopia and in combination with another myopia control products.

Although representative processes and articles have been described in detail herein, those skilled in the art will recognize that various substitutions and modifications may be made without departing from the scope of what is described and defined by the appended claims.

Various embodiments of the invention may be provided according to following statements which may be combined with various of the previously described embodiments of various aspects, in particular of embodiments of the third, the fourth and the fifth aspects: Statement 1: An optical filter system adapted for a spectacle lens, the system comprising a band-cut filter configured to be in a band-cut filter state under a low light condition and not in the band-cut filter state under a high light condition; wherein in the band-cut filter state, the band-cut filter comprises a band-cut filter spectrum comprising a cut band; wherein the low light condition is when an incident light intensity is equal to or lower than a light intensity threshold and the high light condition is when the incident light intensity is higher than the light intensity threshold. Statement 2: The optical filter system of statement 1, wherein the cut band encompasses the wavelengths of 450 nm to 495 nm. Statement 3: The optical filter system of statement 1 or statement 2, further comprising a band-pass filter configured to be in a band-pass filter state under the high light condition and not in the band-pass filter state under the low light condition; wherein in the band-pass filter state the band-bass filter comprises a band-pass filter spectrum comprising a pass band. Statement 4: The optical filter system of statement 3, wherein the pass band encompasses the wavelengths of 450 nm to 495 nm. Statement 5: The optical filter system of any of statements 3 to 4, wherein the pass band and the cut band at least partially overlap. Statement 6: The optical filter system of any of statements 3 to 5, wherein the wavelength range of the incident light intensity at least partially overlaps with the wavelength range of: the cut band, or of the pass band, or of the cut band and the pass band. Statement 7: The optical filter system of any of statements 1 to 6, further comprising a sensor configured to detect the incident light intensity. Statement 8: The optical filter system of statement 7, further comprising a circuit electrically coupled to the sensor, wherein the circuit is coupled to the band-cut filter and configured to set the band-cut filter in or out of the band-cut filter state in accordance with the light intensity threshold. Statement 9: The optical filter system of statement 3 or 4, further comprising: a sensor configured to detect the incident light intensity, and a circuit electrically coupled to the sensor, wherein the circuit is coupled to the band-pass filter and configured to set the band-pass filter in or out of the band-pass filter state in accordance with the light intensity threshold. Statement 10: The optical filter system of any of statements 1 to 9, wherein the light intensity threshold is in the range from 0.33 cd/m2 to 44.4 cd/m2, for example in the range from 5 cd/m2 to 5 cd/m2. Statement 11: The optical filter system of any of statements 11 to 10, wherein the band-cut filter comprises a band-cut filter passive zone and a band-cut filter active zone, wherein the band-cut filter active zone is provided at a periphery of the band-cut filter passive zone. Statement 12: The optical filter system of any of statements 3 to 11, wherein the band-pass filter comprises a band-pass filter passive zone and a band-pass filter active zone, wherein the band-pass filter active zone is provided at a periphery of the band-pass filter passive zone. Statement 13: A spectacle lens comprising the optical filter system of any of statements 1 to 12. Statement 14: An eyewear comprising the optical filter system of any of statements 1 to 13. 15. The eyewear of statement 14, further comprising a spectacle frame and a sensor configured to detect the incident light intensity, wherein the sensor is integrated into the spectacle frame.

The invention claimed is:

1. An illumination system, adapted for an eyewear, comprising:
    a light source configured to emit a first light comprising a power spectrum having full width at half maximum of less than 100 nm in a first range of wavelengths and a second light comprising a power spectrum having full width at half maximum of less than 100 nm in a second range of wavelengths, the power spectrum of the first light and the power spectrum of the second light differ from each other, wherein the light source is further configured to emit pulses of light with a pre-determined time function,
    wherein the pre-determined time function comprises a plurality of packets, wherein each packet of the plurality of packets is followed by a packet interval, which is a clear state, and wherein each packet comprises a pulse alternation between a pulse of the first light and a pulse of the second light, and
    wherein a duration of each packet interval is in a range of 5-20 seconds.

2. The illumination system of claim 1, wherein the pulse alternation is repeated two or more times.

3. The illumination system of claim 1, wherein a duration of each packet is in a range of 1-5 seconds.

4. The illumination system of claim 1, wherein the first range of wavelengths is between 450 nm and 495 nm.

5. The illumination system of claim 1, wherein the second range of wavelengths is between 620 nm and 750 nm.

6. The illumination system of claim 1, further comprising a button configured to switch the light source between, at least:
    an active mode, in which the light source emits pulses of light with the pre-determined time function; and
    an inactive mode, in which the light source does not emit light.

7. An eyewear, comprising a spectacle frame and the illumination system of claim 1.

8. The eyewear of claim 7, further comprising at least one spectacle lens or a pair of spectacle lenses comprising the one spectacle lens, mounted on the spectacle frame.

9. The eyewear of claim 8, wherein the light source of the illumination system is mounted on the spectacle frame or on the spectacle lens.

10. The eyewear of claim 8, wherein the light source of the illumination system and the spectacle lens are configured so that light emitted by the light source of the illumination system is at least partially reflected by the spectacle lens, in a direction to a wearer's eye, when the wearer is wearing the eyewear.

11. The eyewear of claim 7, wherein the light source of the illumination system is configured to emit light in a direction to a wearer's eye, when the wearer is wearing the eyewear.

12. The illumination system of claim 1, wherein a duration of each packet is 2 seconds.

13. The illumination system of claim 1, wherein a duration of each packet interval is 8 seconds.

* * * * *